(12) United States Patent
Powlan

(10) Patent No.: US 9,339,313 B1
(45) Date of Patent: May 17, 2016

(54) HIP FRACTURE SUPPORT PLATE

(71) Applicant: Roy Y. Powlan, Lafayette, CA (US)

(72) Inventor: Roy Y. Powlan, Lafayette, CA (US)

(*) Notice: Subject to any disclaimer, the term of this patent is extended or adjusted under 35 U.S.C. 154(b) by 0 days.

(21) Appl. No.: 14/545,542

(22) Filed: May 20, 2015

(51) Int. Cl.
*A61B 17/74* (2006.01)
*A61B 17/80* (2006.01)
*A61B 17/86* (2006.01)

(52) U.S. Cl.
CPC .............. *A61B 17/746* (2013.01); *A61B 17/74* (2013.01); *A61B 17/8014* (2013.01); *A61B 17/8685* (2013.01)

(58) Field of Classification Search
CPC ..................................................... A61B 17/746
See application file for complete search history.

(56) References Cited

U.S. PATENT DOCUMENTS

| | | | | |
|---|---|---|---|---|
| 4,438,762 A * | 3/1984 | Kyle | .................... | A61B 17/746 606/65 |
| 4,628,923 A | 12/1986 | Medoff | | |
| 4,973,332 A * | 11/1990 | Kummer | .............. | A61B 17/746 606/304 |
| 4,988,350 A | 1/1991 | Herzberg | | |
| 5,190,544 A * | 3/1993 | Chapman | ............... | A61B 17/72 606/280 |
| 5,462,547 A * | 10/1995 | Weigum | ............... | A61B 17/746 606/65 |
| 5,484,439 A * | 1/1996 | Olson | .................. | A61B 17/746 606/65 |
| 7,635,365 B2 * | 12/2009 | Ellis | .................... | A61B 17/8076 606/71 |
| 8,147,493 B2 * | 4/2012 | Dutoit | .................. | A61B 17/746 606/284 |
| 8,177,819 B2 * | 5/2012 | Huebner | ................ | A61B 17/80 606/281 |
| 8,262,709 B1 * | 9/2012 | Powlan | .............. | A61B 17/1728 606/281 |
| 8,579,899 B2 | 11/2013 | Ahmadi | | |
| 8,734,448 B2 | 5/2014 | Thakkar | | |
| 2007/0185493 A1 * | 8/2007 | Feibel | ................ | A61B 17/8061 606/71 |
| 2011/0152943 A1 * | 6/2011 | Gonzalez-Hernandez | ......... | A61B 17/8057 606/286 |
| 2013/0317502 A1 * | 11/2013 | Overes | .................... | A61B 17/74 606/66 |
| 2014/0378973 A1 * | 12/2014 | Mueckter | ............... | A61B 17/72 606/64 |
| 2015/0250507 A1 * | 9/2015 | Harrison | ............ | A61B 17/8061 606/66 |

FOREIGN PATENT DOCUMENTS

FR 2712173 A1 * 5/1995 ........... A61B 17/746

OTHER PUBLICATIONS

Richard f. Kyle, Thomas A. Russell, Andrew N. Pollak, American Academy of Orthopedic Surgeons; News; AAOS Now. SpotCheck: Intertrochanteric Fracture Treatment.

* cited by examiner

Primary Examiner — David Bates

(57) ABSTRACT

A hip fracture support plate, in combination with hip screw fixation of an intertrochanteric hip fracture, provides additional support of the femoral head and neck fragment, tending to reduce hip screw cut-out or fracture, with collapse and mal-union of the head and neck.

9 Claims, 5 Drawing Sheets

HIP FRACTURE SUPPORT PLATE

FIELD OF THE INVENTION

This invention generally relates to the surgical treatment of fractures of the hip, specifically, intertrochanteric fractures of the hip, and to an orthopedic device to promote their healing.

BACKGROUND OF THE INVENTION

The sliding hip screw, a widely used device for treating for treating intertrochanteric fractures, consists of a lag screw which is inserted across the fracture into the head and neck of the femur, and a femoral side plate with a tubular support through which the trailing end of the screw can slide when healing with some shorting of the bone takes place.

Effective as these hip screws are however, they have some problems. Failure of healing in proper alignment occurs in a significant percentage of fractures treated this way because of complications arising from, for example, excessive pressure such as weight bearing on an osteoporotic femoral head, or sub-optimal positioning of the nail, which results in the threaded tip of the screw cutting out of the femoral head, or breakage of the nail, all of which can result in a severe displacement of the head and neck fragment, necessitating further reconstructive surgery, often hip replacement. The increased morbidity and mortality resulting from these complications suggests the need for further improvement in the treatment of these difficult fractures.

It is the aim of the present invention to provide additional support of the femoral head and neck fragment of the fracture, and to significantly alleviate the results of the downward pressure on the hip screw by transferring some of the pressure from the hip screw to the present device, a hip fracture support plate, thereby altering the relationship between the forces tending to displace the head and neck fragment, and the devices that are resisting these forces, resulting in a reduction of the complications arising from the use of sliding hip screw fixation alone.

SUMMARY OF THE INVENTION

The present invention comprises an elongate rigid plate, one end of which, the first, anchoring end, is adjustably and releasably fastened to the side-plate of a previously inserted sliding hip screw. The elongate body of the plate and the opposite, tapered, twisted, supporting second end are configured to enable the support plate to be positioned beneath and slightly hooked around the ligamentous capsule surrounding the hip joint and the inferior surface of the neck of the femur, thereby enabling the hip joint support plate to stabilize and support the head and fractured base of the neck of the femur. As a result, a portion of the load of the head and neck is transferred from the sliding hip screw, through the hip fracture support plate to the sliding hip screw side-plate and ultimately to the cortical bone of the femoral shaft, decreasing the tendency toward sliding hip screw complications. The fracture support plate also helps prevent rotation of the head and neck fragment around a single sliding hip screw while healing is taking place.

Following the anatomic or near anatomic reduction of the fracture, and the insertion of a sliding hip screw or similar, and the fixation of its supporting side-plate to the lateral cortex of the bone by means of bone screws placed through chamfered openings to ensure that the screw heads are flush with the surface, access to the anterior and inferior surfaces of the ligamentous capsule of the femoral neck is then used to rotate and slide the tapered and twisted second supporting end of the hip fracture support plate to beneath the ligamentous capsule of the hip joint, and become positioned beneath it.

The first, anchoring end of the hip fracture support plate is then fastened to the side-plate of an already inserted sliding hip screw, and to the femoral shaft using bone screws placed in appropriately located elongate openings in the fracture support plate.

The openings for the bone screws are elongate to permit the support plate to be adjusted proximally or distally before the bone screws are tightened, enabling a snug fit of the support plate beneath the joint capsule.

A longitudinal lip along the outer edge of the first, anchoring end of the hip support plate, corresponding to the edge of the side-plate of the sliding hip screw, prevents rotation of the support plate on the hip screw plate when they are locked in place together, strengthening the construct. Both plates are longitudinally concave to conform to the convexity of the femoral cortex, which helps resist bending.

The hip fracture support plate and a mirror image of it, are configured for use with both right and left hips, and the overall dimensions and thickness are predetermined.

In another embodiment of the device, the first, anchoring end of the hip support plate is extended proximally so as to become positioned alongside the greater trochanter of the proximal femur to function additionally as a trochanteric stabilizing plate, having a plurality of openings for screw fixation to the trochanter.

DETAILED DESCRIPTION OF THE DRAWINGS

Figure 1:
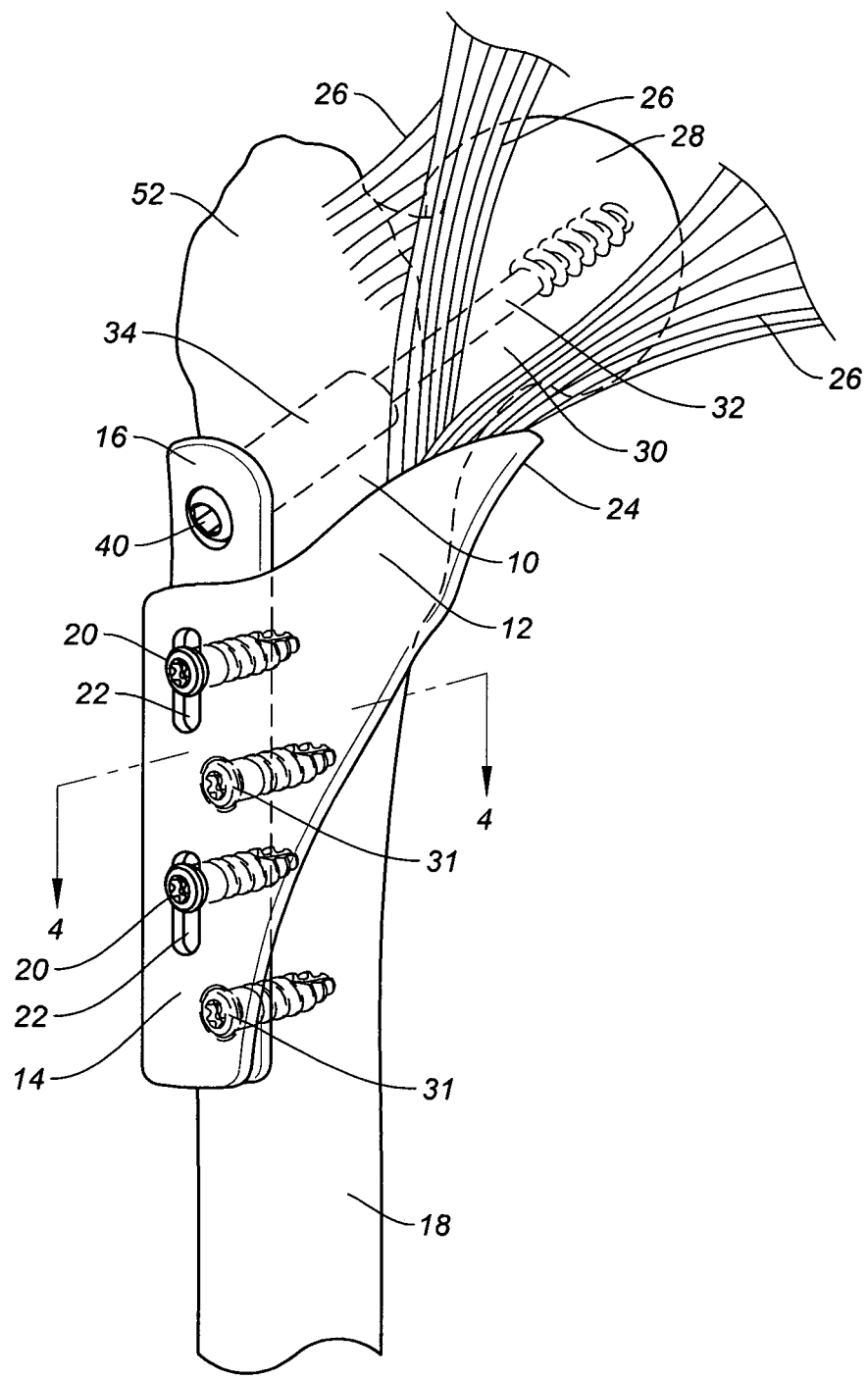
FIG. 1 is a perspective view of the device applied to a proximal femur.

FIG. 1 is a perspective view of a proximal femur 10 with the first anchoring end 14 of the device 12 attached to a hip screw side plate 16 and the underlying femoral shaft 18, by means of screws 20, through the elongated openings 22. The elongated openings 22, allow the device 12 to slide up and down before the screws 20 are tightened. This enables the second supporting end 24 of the device 12 to be urged upwards tightly beneath the ligamentous hip capsule 26 which surrounds the head 28 and neck 30 of the proximal femur 10, and to provide support to the head and neck.

The screws 31 attach the sliding hip screw side plate 16 to the femoral shaft 18.

A commonly used sliding hip screw 32 and its sleeve 34, are shown inserted in the head and neck, 28 and 30 of the femur 10.

Figure 2:
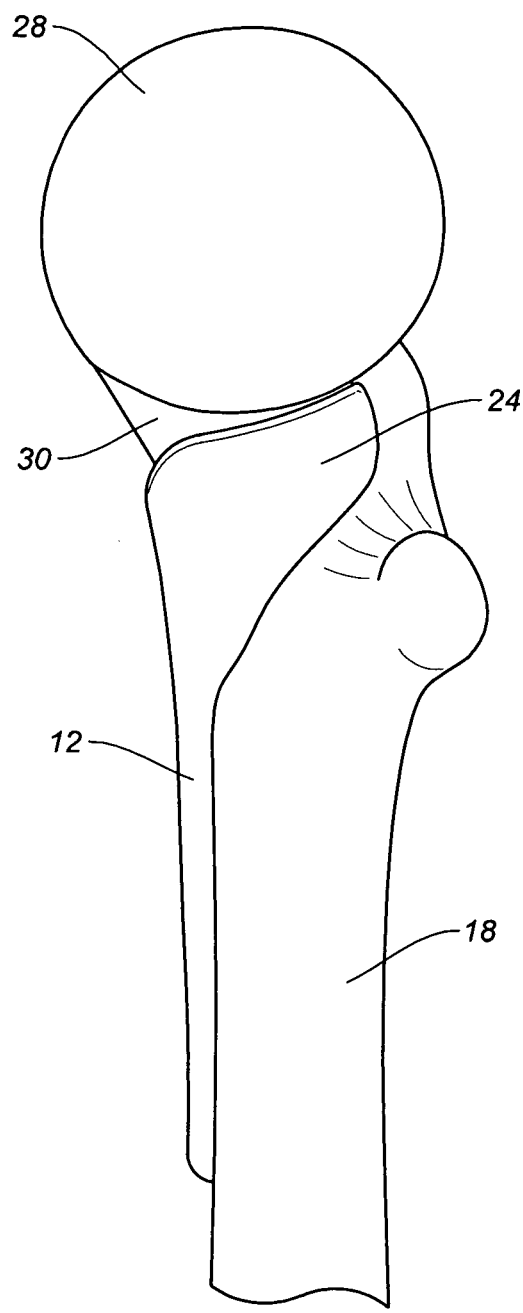
FIG. 2 is rear view of the device applied to a proximal femur.

FIG. 2 is a view of the medial surface of the head 28, neck 30, and the femoral shaft 18 as seen from the midline of the body. It shows the device 12 and its second supporting end 24 beneath and partially encircling the femoral neck 30. The second supporting end 24, of the fracture plate 12 is twisted approximately 35 degrees from the horizontal plane to become roughly parallel to the angle of the neck 30. This enables broadly surfaced, efficient support of the base of the neck and any related bone fragments while bone healing takes place.

Figure 3:
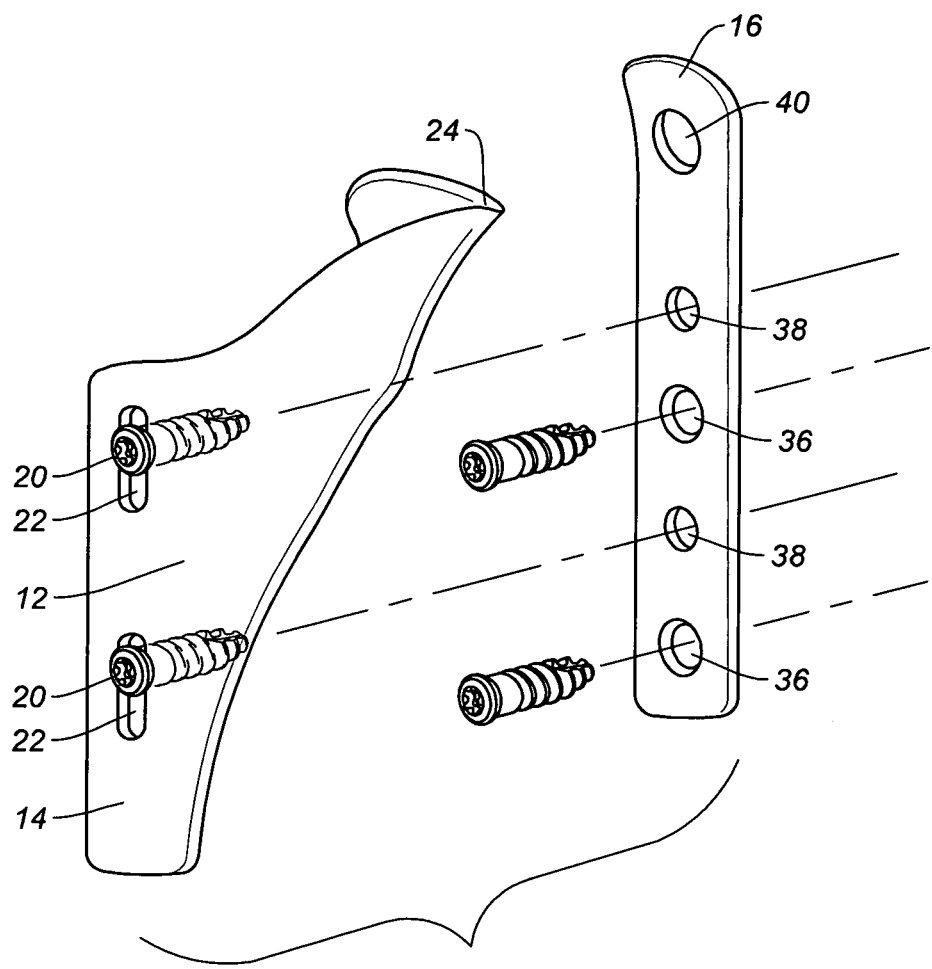
FIG. 3 is an exploded perspective view of the device.

FIG. 3 incl. FIG. 1 is an exploded perspective view showing the device 12 and the sliding hip screw side-plate, 16, together with the bone screws 20 and 31, used to fasten both to the femoral cortex 18. The device 12 has a broad anchoring base 14 with elongate screw openings 22 as in FIG. 1. The body of the device 12 is curved to wrap around the underlying sliding hip screw side-plate 16, the anterior surface of the intertrochanteric area of the hip, and to beneath the ligamentous hip capsule 26, through an angle around the vertical axis of approximately 180 degrees as shown in FIG. 1. The second supporting end 24, is tapered and twisted to conform to the undersurface of the ligamentous capsule 26 of the neck of the hip 30.

The first, anchoring end 14 of the fracture support plate 12, has elongate openings 22, and screws 20, to enable sliding adjustment of the plate. The screws are tightened after the second supporting end 24 of the plate 12, has been positioned snugly under the ligamentous hip capsule 26. The sliding hip screw side-plate 16, has two chamfered openings 36, and screws 31, for fixation of the plate to the femoral cortex 18. It also has two openings 38, enabling the fixation of the fracture support plate 12 to the femoral cortex 18 with screws 20. An opening 40, in plate 16 provides for a sliding hip screw 32.

Figure 4:
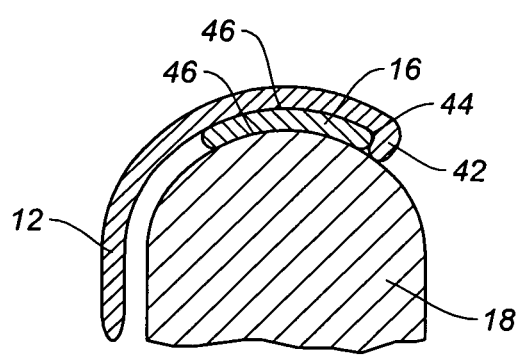
FIG. 4 is a cross-sectional view of the device and the underlying bone.

FIG. 4 is a cross-sectional view of the device 12, the sideplate of the sliding hip screw 16, and the underlying femoral bone 18. It shows the concavity 46 of both plates to conform to the convexity of the bone's surface. It also shows the lip 42 along the longitudinal edge of the hip fracture support plate 12, that conforms to the longitudinal edge 44 of the side-plate 16 of the sliding hip screw 32. The lip 42 lessens the tendency of the of the fracture support plate 12, to rotate on the underlying sliding screw plate 16 when they are tightly bound together with bone screws 20,31.

Figure 5:
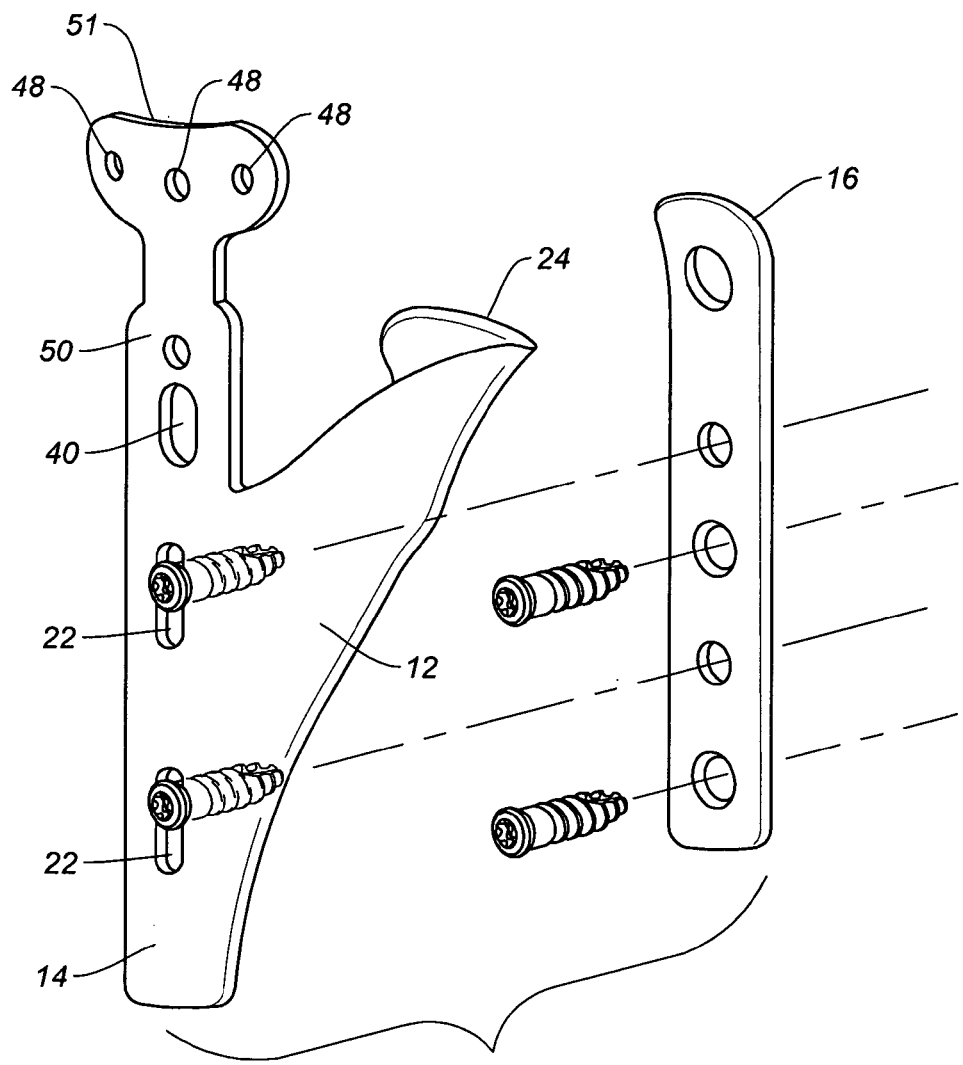
FIG. 5 is a perspective view of another embodiment of the device.

FIG. 5 in FIG. 1 is a perspective view of another embodiment of the device 12. The first, anchoring end 14 of the device 12 has a proximal extension 50, which, with its top end 51 are bendable and are enabled to be configured to engage with the surface of the greater trochanter 52 of the proximal femur 10 and to buttress the trochanter. The top end 51 of extension 50 has attachment apertures 48 for attachment of the extension to the trochanter, and an opening 40 for a sliding hip crew. This embodiment of the device 12 which buttresses the greater trochanter 52 as well as supporting the head 28 and neck 30 of the femur 10, helps prevent the collapse of certain unstable intertrochanteric fractures.

DRAWINGS REFERENCE NUMERALS WORKSHEET

10 Proximal Femur
12 Device, Hip Fracture Support Plate
14 First, anchoring end of device
16 Sliding hip screw plate
18 Femoral shaft
20 Screws
22 Elongate openings
24 Second, supporting end of device
26 Ligamentous hip capsule
28 Head of femur
30 Neck of femur. 31 Screws
32 Sliding hip screw
34 Sliding hip screw sleeve
36 Chamfered openings
38 Screw openings
40 Opening for sliding hip screw
42 Lip of fracture support plate
44 Longitudinal edge of sliding hip screw plate
46 Concavity of both plates
48 Attachment apertures
50 Proximal extension of anchoring end of fracture support plate
51 Top end of proximal extension of device. 52 Greater Trochanter

I claim:

1. A device for treating an intertrochanteric fracture of a proximal end of a femur in the area of a hip joint, comprising:
   an elongate sliding screw plate for longitudinal fixation to a femoral shaft of the femur,
      said sliding screw plate comprising openings enabling fixation to said femoral shaft,
      said screw plate further comprising a sleeve positioned angularly at an end of said sliding screw plate towards the proximal end of the femur, said sleeve enabling insertion of a connecting member into a femoral head of the femur,
   an elongate hip fracture support plate for separable connection with said sliding screw plate, said hip fracture support plate comprising two ends, a first, anchoring end and a second, supporting end,
      wherein said first anchoring end comprises an elongate generally rectangular configuration,
      wherein said anchoring end comprises a plurality of slotted openings, said slotted openings corresponding to said openings of said sliding screw plate enabling a slidingly adjustable bone screw fixation of said rectangular first anchoring end of said hip fracture support plate to said sliding screw plate and to said femoral shaft,
      wherein said first anchoring end of said fracture support plate substantially exists within a first plane, said first plane corresponding to a sagittal plane of a lateral cortex of said proximal femur,
      wherein said supporting end comprises an elongate twisting spiral configuration,
      wherein a distal end of said supporting end of said hip fracture support plate a tongue-like tab, said tab substantially existing in a second plane, said second plane corresponding to the medial proximal femoral cortex, and being substantially parallel to said first plane, thereby enabling the anchoring end of the hip fracture support plate to support fractured fragments of the intertrochanteric fracture, and with said configuration enabling said second end of said hip fracture support plate to conform to an anatomic configuration of anterior and inferior portions of said hip joint and its ligamentous capsule, whereby a portion of the forces causing said connecting member in the head of the femur to cut-out or break, and the head of the femur to rotate on the connecting member is distributed to the hip fracture support plate, diminishing the possibility of sliding hip screw failure.

2. The device according to claim 1, wherein said anchoring end is generally congruent with said elongate sliding screw plate, and with a longitudinal edge of said anchoring end of said fracture support plate corresponding to a longitudinal edge of said elongate sliding screw plate and comprising a longitudinal bend, said bend enabling a sliding translation and prevention of rotation of the hip fracture supporting plate on the underlying sliding screw plate.

3. The device according to claim 1, wherein the elongate generally rectangular first anchoring end of the hip fracture support plate and the sliding screw plate comprise longitudinally concave surfaces, enabling conformity to a convexity of the proximal femoral cortex and an increased resistance to bending.

4. The device according to claim 1, wherein the openings in the sliding screw plate are chamfered openings enabling flush screw fixation of said sliding screw plate to the femoral shaft.

5. The device according to claim 1, wherein the fracture support plate comprises a bioinert material including one of stainless steel or titanium.

6. The device according to claim 1, wherein the fracture support plate comprises a predetermined size and thickness.

7. The device according to claim 1, wherein the first, anchoring end of the hip fracture support plate comprises an elongate extension, said elongate extension configured to engage with a lateral surface of a greater trochanter of the femur and to buttress said trochanter, and with said extension comprising a plurality of attachment apertures.

8. A method of treating intertrochanteric fractures of the hip comprising:
   (a) providing an elongate sliding screw plate with angularly attached sleeve, the screw plate attached to the cortex of a proximal femur,
   (b) choosing an elongate hip fracture support plate with a first, anchoring end and a second, supporting end comprising a tapered twisting spiral configuration, the supporting end comprising a plurality of slotted openings,
   (c) inserting and rotating the second supporting end of the hip fracture support plate around the sliding screw plate, across an anterior surface of the proximal femur, into a space beneath a ligamentous capsule of the hip joint,
   (d) aligning the first anchoring end of the hip fracture support plate with the underlying sliding screw plate with longitudinal edges of each of the plates engaged to one another,
   (e) inserting locking screws through the elongate openings in the fracture support plate to engage both plates together loosely,
   (f) translating the second supporting end of the fracture support plate tightly beneath the ligamentous capsule, and
   (g) tightening the fracture support plate screws.

9. A method of treating intertrochanteric fractures of the hip comprising:
   (a) providing an elongate sliding screw plate with angularly attached sleeve, the screw plate attached to the cortex of a proximal femur,
   (b) choosing an elongate hip fracture support plate with a first, anchoring end and a second, supporting end comprising a tapered twisting spiral configuration, the supporting end comprising a plurality of elongate openings, and the anchoring end comprising a proximal extension,
   (c) inserting and rotating the second supporting end of the hip fracture support plate around the sliding screw plate, across an anterior surface of the proximal femur, into a space beneath a ligamentous capsule of the hip joint,
   (d) aligning the first anchoring end of the hip fracture support plate with the underlying sliding screw plate with longitudinal edges of each of the plates engaged to one another,
   (e) inserting locking screws through the elongate openings in the hip fracture support plate to engage both plates loosely,
   (f) translating the second supporting end of the hip fracture support plate tightly beneath the ligamentous capsule,
   (g) tightening the hip fracture support plate screws,
   (h) configuring a superior end of the proximal extension of the first anchoring end of the hip fracture support plate to conform to a greater trochanter of the femur, and
   (i) attaching the superior end of the proximal extension of the first anchoring end of the hip fracture support plate to the greater trochanter with fasteners.

\* \* \* \* \*